(12) United States Patent
Bui et al.

(10) Patent No.: US 9,040,027 B2
(45) Date of Patent: *May 26, 2015

(54) COMPOSITIONS CONTAINING A MICRONIZED WAX

(75) Inventors: Hy Si Bui, Piscataway, NJ (US); Anita Chon Tong, Westfield, NJ (US); Susan Halpern, Basking Ridge, NJ (US); Mohamed Kanji, Edison, NJ (US); Fatima Ramadan, Marlboro, NJ (US); Yoriko Kawaratani, Tokyo-to (JP); Nishith Patel, Roselle Park, NJ (US); Ram Hariharan, Springfield, NJ (US)

(73) Assignee: L'Oréal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/341,597

(22) Filed: Dec. 30, 2011

(65) Prior Publication Data

US 2012/0171142 A1 Jul. 5, 2012

Related U.S. Application Data

(60) Provisional application No. 61/428,523, filed on Dec. 30, 2010.

(51) Int. Cl.
| | |
|---|---|
| *A61K 8/92* | (2006.01) |
| *A61Q 1/04* | (2006.01) |
| *A61K 8/04* | (2006.01) |
| *A61K 8/31* | (2006.01) |
| *A61Q 1/02* | (2006.01) |
| *A61K 8/81* | (2006.01) |

(52) U.S. Cl.
CPC . *A61K 8/044* (2013.01); *A61K 8/31* (2013.01); *A61Q 1/02* (2013.01); *A61Q 1/04* (2013.01); *A61K 8/8111* (2013.01); *A61K 8/925* (2013.01)

(58) Field of Classification Search
CPC .............. A61K 2800/412; A61K 8/31; A61K 2800/92; A61K 8/375; A61K 8/678; A61K 8/8152; A61K 8/8182; A61K 8/92; A61K 8/922; A61K 8/925; A61K 8/927; A61K 9/0014; A61K 8/361; A61K 8/37; A61K 8/39
See application file for complete search history.

(56) References Cited

U.S. PATENT DOCUMENTS

| | | | |
|---|---|---|---|
| 7,008,619 B2 * | 3/2006 | Kanji | 424/70.7 |
| 2005/0169949 A1 * | 8/2005 | De La Poterie et al. | 424/401 |
| 2009/0311296 A1 * | 12/2009 | Tarasi et al. | 424/401 |
| 2013/0101542 A1 | 4/2013 | Bui et al. | |
| 2013/0130959 A1 | 5/2013 | Li et al. | |

OTHER PUBLICATIONS

U.S. Appl. No. 13/340,237, filed Dec. 29, 2011, Bui, et al.
U.S. Appl. No. 13/341,514, filed Dec. 30, 2011, Bui, et al.
U.S. Appl. No. 13/884,518, filed May 9, 2013, Kanji, et al.
U.S. Appl. No. 13/884,153, filed May 8, 2013, Li, et al.
U.S. Appl. No. 13/884,122, filed May 8, 2013, Li, et al.
U.S. Appl. No. 13/696,159, filed Jan. 24, 2013, Tong, et al.
U.S. Appl. No. 13/988,630, filed May 21, 2013, Li, et al.

* cited by examiner

*Primary Examiner* — Audrea Buckley
(74) *Attorney, Agent, or Firm* — Oblon, McClelland, Maier & Neustadt, L.L.P.

(57) ABSTRACT

The invention relates to a composition comprising at least one oil-dispersible micronized wax which, if desired, can be processed at room temperature.

11 Claims, No Drawings

COMPOSITIONS CONTAINING A MICRONIZED WAX

CROSS REFERENCE TO RELATED APPLICATION

This application claims the benefit of priority under 35 U.S.C. §119(e) from U.S. Provisional Application Ser. No. 61/428,523, filed Dec. 30, 2010, the entire contents of which is hereby incorporated by reference.

FIELD OF THE INVENTION

The present invention relates to compositions comprising at least one micronized wax. The compositions have beneficial cosmetic properties including comfort upon application and minimized feathering/migration properties, minimized tackiness and/or improved shine properties, and are easily prepared at or about room temperature.

DISCUSSION OF THE BACKGROUND

Generally speaking, high shine compositions such as lip compositions such as lip sticks or lip glosses focus on providing high shine performance while attempting to reduce feathering/migration and/or to reduce tackiness or sticky feeling upon application. However, it is difficult to minimize feathering/migration without having a sticky/tacky feel upon application, particularly in high gloss or shine compositions.

In the past, some formulations have used high amounts of thick oils to achieve high shine in compositions like lip compositions. However, these formulations tend to be very sticky/tacky and do not convey much comfort.

In the past, some formulations have used silica or other gelling agents to hold oils in place and, thus, reduce feathering/migration. Such formulations did not negatively affect shine properties. However, such formulations were sticky/tacky upon application and sometimes even had a stringy appearance between lips.

Also in the past, some formulations used waxes or other structuring agents to hold oils in place and reduce feathering/migration. These formulations added creaminess to the texture but did not have good shine properties.

With respect to foundations, although shine is not a particularly favorable characteristic for such cosmetic products, good feel upon application (smooth, not tacky) and good stay, holding power, and/or transfer-resistance are desirable properties. However, it is difficult to produce a composition having both good feel upon application, good end look, and minimized sticky/tacky/draggy feeling.

There is thus a need to develop a cosmetic composition, in particular for making up keratin materials such as the lips, making it possible to provide high shine or gloss properties while at the same time reducing the amount of feathering/migration and reducing the amount of tackiness/stickiness upon application.

There is a further need to develop a cosmetic composition, in particular for making up keratin materials such as skin, making it possible to have a transfer resistant product while at the same time reducing the amount of tackiness/stickiness/drag upon application.

SUMMARY OF THE INVENTION

The present invention relates to compositions for keratin materials comprising at least one micronized. Preferably, the composition is anhydrous.

The present invention also relates to methods of treating, caring for and/or making up keratin materials by applying compositions of the present invention to keratin materials in an amount sufficient to treat, care for and/or make up the keratin materials. Preferably, the composition is anhydrous.

The present invention also relates to methods of improving the shine or gloss properties of a composition for keratin materials, comprising adding to the composition at least one micronized wax. Preferably, the composition is anhydrous.

The present invention also relates to methods of reducing feathering or migration of a composition for keratin materials, comprising adding to the composition at least one micronized wax. Preferably, the composition is anhydrous.

The present invention also relates to methods of reducing stickiness or tackiness of a composition for keratin materials, comprising adding to the composition at least one micronized wax. Preferably, the composition is anhydrous.

The present invention also relates to methods of preparing compositions at low temperatures (approximately room temperature) by adding at least one micronized wax to at least one oil and mixing the oil and wax to form an anhydrous composition comprising at least one micronized wax.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Keratinous material" as used herein includes any material containing keratin such as, for example, lips, hair, eyelashes, skin, fingernails, etc.

"Composition for keratinous material" as used herein can be any composition for application to any keratinous material such as, for example, a composition for application to lips such as a lipstick or lip gloss, and a composition for application to skin such as a moisturizer or a foundation.

"Film former" or "film forming agent" as used herein means a polymer or resin that leaves a film on the substrate to which it is applied, for example, after a solvent accompanying the film former has evaporated, absorbed into and/or dissipated on the substrate.

"Anhydrous" means the compositions contain less than 1% water. "Substantially anhydrous" means that the compositions contain less than 3% water (or lacks sufficient water to form an emulsion). Preferably, the compositions of the present invention comprising the at least one micronized wax contain no water.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

Micronized Wax

According to the present invention, compositions comprising at least one micronized wax are provided. The micronized wax of the present invention is non-liquid at room temperature (25° C.) and atmospheric pressure. According to preferred embodiments, the at least one micronized wax is spherical. Particles of the micronized wax of the present invention have a diameter on the order of 1,000 micrometers or less. According to preferred embodiments, the external diameter is in a range between about 0.20 and 1,000 micrometers, preferably between about 1 and 500 micrometers, preferably between about 3 and 200 micrometers, and preferably between about 5 and 50 micrometers, including all ranges and subranges therebetween.

According to preferred embodiments of the present invention, the at least one micronized wax is oil-dispersible. "Oil-dispersible" is understood to mean that the at least one micronized wax is dispersed in an oil or a mixture of oils such that at least 50% of the wax has been dispersed, preferably 60%, preferably 70%, preferably 80%, preferably 90%, preferably 95%, and preferably 100%, including all ranges and subranges therebetween.

According to preferred embodiments, the micronized wax is hollow. The wax of the present invention may contain, if desired, suitable chemical and/or biological agents.

Suitable micronized waxes of the present invention include those described in U.S. patent application publication no. 2009/0311296, the contents of which are hereby incorporated by reference in their entirety. Commercially available suitable waxes include Universal Remediation's Bioboom product.

According to preferred embodiments, the at least one micronized wax is present in compositions for application to lips in an amount ranging from about 2-45% by weight, more preferably from about 5-30% by weight, more preferably from about 7-20% by weight based on the total weight of the composition, including all ranges and subranges within these ranges.

According to preferred embodiments, the at least one micronized wax is present in compositions for application to skin in an amount ranging from about 1-25% by weight, more preferably from about 3-15% by weight, more preferably from about 5-10% by weight based on the total weight of the composition, including all ranges and subranges within these ranges.

Generally speaking, the at least one micronized wax is present in compositions for application to keratinous materials in an amount ranging from about 1-45% by weight, more preferably from about 3-30% by weight, more preferably from about 5-20% by weight based on the total weight of the composition, including all ranges and subranges within these ranges.

According to preferred embodiments, if other wax(es) are present in the composition, the micronized wax constitutes the main wax of the composition (that is, the composition contains more micronized wax than all other waxes combined on a weight basis, containing, for example, 51%, 60%, 70%, 80%, 90%, 95% micronized wax as compared to all other waxes present on a weight basis). According to a preferred embodiment, the composition contains micronized wax of the present invention but no other waxes.

Oil

According to the present invention, compositions comprising at least one oil in addition to the at least one micronized wax are provided.

Suitable oils include volatile and/or non-volatile oils. Such oils can be any acceptable oil including but not limited to silicone oils and/or hydrocarbon oils.

According to certain embodiments, the oil carrier comprises one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other embodiments, the oil carrier comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to other embodiments of the present invention, the oil carrier comprises at least one non-volatile oil. Examples of non-volatile oils that may be used in the present invention include, but are not limited to, polar oils such as:

—hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

—synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

—synthetic ethers containing from 10 to 40 carbon atoms;

—$C_8$ to $C_{26}$ fatty alcohols, for instance oleyl alcohol, cetyl alcohol, stearyl alcohol, and cetearly alcohol; and —mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

In accordance with the present invention, volatile hydrocarbons such as isododecane are particularly preferred.

According to preferred embodiments, the oil(s) is (are) present in compositions for application to lips in a combined amount sufficient to disperse (as discussed above) the micronized wax. Typically, the amount of oil present in the compositions of the present invention ranges from about 10-70% by weight, more preferably from 15-65% by weight, more preferably from about 20-60% by weight based on the total weight of the composition, including all ranges and subranges within these ranges.

According to preferred embodiments, the oil(s) is(are) present in compositions for application to skin in a combined amount sufficient to disperse (as discussed above) the micronized wax. Typically, the amount of oil present in the compositions of the present invention ranges from about 10-80% by weight, more preferably from 20-70% by weight, more preferably from about 30-60% by weight based on the total weight of the composition, including all ranges and subranges within these ranges.

Generally speaking, the at least one oil is present in compositions for application to keratinous materials in an amount ranging from about 10-80% by weight, more preferably from about 15-70% by weight, more preferably from about 20-60% by weight based on the total weight of the composition, including all ranges and subranges within these ranges.

Compositions of the present invention can optionally further comprise any additive usually used in the field(s) under consideration. For example, dispersants such as poly(12-hydroxystearic acid), antioxidants, sunscreens, preserving agents, particularly phenoxyethanol, fragrances, fibers, fillers, neutralizing agents, cosmetic and dermatological active agents such as, for example, emollients, moisturizers, vitamins, essential fatty acids, surfactants, silicone elastomers, pasty compounds, viscosity increasing agents such as additional waxes (for example, soft or adhesive waxes) or liposoluble/lipodispersible polymers, film forming agents, colorants, and mixtures thereof can be added. A non-exhaustive listing of such ingredients can be found in U.S. patent application publication nos. 2004/0170586 and 2009/0142289, the entire contents of which are hereby incorporated by reference. Further examples of suitable additional components can be found in the other references which have been incorporated by reference in this application. Still further examples of such additional ingredients may be found in the *International Cosmetic Ingredient Dictionary and Handbook* (9$^{th}$ ed. 2002).

According to preferred embodiments of the present invention, the compositions can further comprise a desired agent. The desired agent can be, for example, any colorant (pigment, dye, etc.), any pharmaceutically or cosmetically active agent, or any film forming agent known in the art. For example, a cosmetic makeup composition comprising colorant can provide colorant and/or film forming agent to a substrate (eyelash) during use to provide the substrate with the desired film and/or color. Similarly, a pharmaceutical or cosmetic composition comprising a pharmaceutically active agent can provide such active agent to the patient or consumer upon use.

Acceptable colorants include pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine and barium.

A particularly preferred colorant is a carbon black dispersion given its ability to be processed at low temperatures.

Acceptable film forming agents and/or rheological agents are known in the art and include, but are not limited to, those disclosed in U.S. patent application publication no. 2004/0170586, the entire contents of which is hereby incorporated by reference.

Non-limiting representative examples of acceptable film forming/rheolgocial agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film forming/rheological agents also include water soluble polymers such as, for example, high molecular weight crosslinked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropyltrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof.

In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

According to other preferred embodiments, methods of treating, caring for and/or enhancing the appearance of a keratinous material by applying compositions of the present invention to the keratinous material in an amount sufficient to treat, care for and/or enhance the appearance of the keratinous material are provided. In accordance with these preceding preferred embodiments, the compositions of the present invention are applied topically to the desired area in an amount sufficient to treat, care for and/or enhance the appearance of the keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag or tackiness), reduced migration or feathering, and/or increased shine wear properties are provided.

According to other embodiments of the present invention, methods of improving the shine or gloss properties of a composition, comprising adding at least one oil-dispersible micronized wax to the composition are provided.

According to preferred embodiments of the present invention, the compositions described above can be prepared at low temperatures (approximately room temperature) by adding the components of the composition in a vessel and agitating the vessel to distribute the components. For example, the micronized wax can be added to an oil such as isododecane to disperse the wax in the oil to form a composition comprising the dispersed micronized wax.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1-6

| Chemical Name | Comparative example 1 | Inventive example 2 | Inventive example 3 | Inventive example 4 | Inventive example 5 | Inventive example 6 |
|---|---|---|---|---|---|---|
| Bioboom | | 5.50 | 5.50 | 10.50 | 15.75 | 25.75 |
| Synthetic beeswax | 5.50 | | | | | |
| Silica dimethyl silylate | 4.00 | 4.00 | 1.00 | | | |
| Polybutene | QS | QS | QS | QS | QS | QS |
| bis-diglyceryl polyacyladipate-2 | 12.34 | 12.34 | 13.16 | 12.34 | 12.34 | 12.34 |
| Isoeicosane | 5.22 | 5.22 | 5.57 | 5.22 | 5.22 | 5.22 |
| Stearyl heptanoate | 4.75 | 4.75 | 5.06 | 4.75 | 4.75 | 4.75 |
| Diisopropyl dimer dilinoleate | 4.30 | 4.30 | 4.59 | 4.30 | 4.30 | 4.30 |
| Vp/hexadecene copolymer | 30.00 | 30.00 | 30.00 | 30.00 | 30.00 | 30.00 |
| Microcrystalline wax | 1.00 | 1.00 | 1.00 | | | |
| Aluminum starch octenylsuccinate | 3.00 | 3.00 | 3.00 | 3.00 | 3.00 | 3.00 |
| Silica | 5.25 | 5.25 | 5.25 | 5.25 | | |
| PENTAERYTHRITYL TETRAISOSTEARATE | [12] | [12] | [12] | [12] | [12] | [12] |
| Pigment | 2.00 | 2.00 | 2.00 | 2.00 | 2.00 | 2.00 |
| Mica | 3.00 | 3.00 | 3.00 | 3.00 | 3.00 | 3.00 |

Procedure

For each composition, all ingredients were added to a suitable side metal container. The contents were heated to 90 Celsius degrees and mixed with a propeller blade until homogeneous.

It was heated for at most 1 hour and then cooled down with continuous agitation until 40 Celsius degrees and the contents were poured to suitable size container for evaluation.

Invention example 2 which contained micronized wax at 5.5% and fumed silica at 4%. It was very shiny. Its initial application was slightly heavy but it had little tack/sticky feel on lips. It had minimum feathering/migration after 1 hr.

Invention Example 3 which contained micronized wax at 5.5% and fumed silica at 1%. It was very shiny. Its application was smooth and had very little tack/sticky feel on lips. It had minimum feathering/migration after 1 hr.

Comparative Example 1 which contained beeswax at 5.5% and fumed silica at 4%. It was very shiny. Its application was smooth but had tack/sticky feel on lips. It had a bad feathering/migration after 1 hr.

This comparison illustrates that by replacing beeswax with micronized wax of the present invention in a lip gloss formula, feathering/migration properties were improved and sticky/tacky feel was reduced while maintaining high shine.

EXAMPLE 7

Lip Gloss Ambient Processing

Composition

| Chemical name | Inventive example 7 |
|---|---|
| Micronized beeswax/isododecane | 47.53 |
| Polyisobutene | 8.23 |
| Isododecane | 0.84 |
| pentaerythrityl tetraisostearate | 4.89 |

-continued

| Chemical name | Inventive example 7 |
|---|---|
| Octyldodecanol | 6.7 |
| tridecyl trimellitate | 30.01 |
| Pigment/Pearl | 1.82 |
| Total | 100 |

Procedure

At ambient condition, micronized beeswax was predissolved in isododecane until contents were smooth. Afterward all ingredients were added to a suitable size metal container and mixed with a cowls blade until texture is smooth and contents were uniform. The mixing speed was set at 800 rpm. Once all contents were uniform and the texture is smooth, they were poured into containers for further evaluations.

Inventive example 7 was able to form a shiny lip gloss without high temperature processing while maintaining the integrity of traditional lip gloss functions. It was also surprisingly not tacky or sticky unlike conventional lip glosses which becomes sticky or tacky overtimes.

EXAMPLE 8

Foundation

| | Chemical Name | 100.000 Inventive Ex. A % wt/wt | 100.000 Comparative Ex. B | bal %: |
|---|---|---|---|---|
| A | Isododecane | 45 | 45 | % |
| | Dimethicone (2 cst) | 17 | 17 | % |
| | BioBoom | 25 | | % |
| | Beeswax | | 25 | |
| | Silica | 3 | 3 | % |
| | TITANIUM DIOXIDE (and) DISODIUM STEAROYL GLUTAMATE (and) ALUMINUM HYDROXIDE | 8 | 8 | % |
| | IRON OXIDES (and) DISODIUM STEAROYL GLUTAMATE (and) ALUMINUM HYDROXIDE | 1.4 | 1.4 | % |
| | IRON OXIDES (and) DISODIUM STEAROYL GLUTAMATE (and) ALUMINUM HYDROXIDE | 0.4 | 0.4 | % |
| | IRON OXIDES (and) DISODIUM STEAROYL GLUTAMATE (and) ALUMINUM HYDROXIDE | 0.2 | 0.2 | % |

Procedure:
1. In container A, mix BioBoom (room temperature) or Beeswax (high temperature) at medium/high sheer in oil solvents until fully dissolved.
2. Add pre-prepared pigment grind TITANIUM DIOXIDE (and) DISODIUM STEAROYL GLUTAMATE (and) ALUMINUM HYDROXIDE and the IRON OXIDES (and) DISODIUM STEAROYL GLUTAMATE (and) ALUMINUM HYDROXIDES with Isododecane- mixing at high sheer (1000 rpm)
3. Mix for 30 min at current temperature
4. Mix until batch is cool (Comparative Ex)

COMPARISON

Inventive Example A compared to Comparative Example B showed improved cosmetic properties including higher transfer resistance, better feel, enhanced spreadability and more even end look.

What is claimed is:

1. A composition comprising at least one oil-dispersible micronized wax in an amount of 5 to 30% by weight, and 20 to 60% by weight of at least one volatile hydrocarbon oil and wherein the composition is in the form of a lip composition, wherein the micronized wax is a micronized beeswax, a micronized soy wax, or a combination thereof.

2. The composition of claim 1, in the form of a lip gloss.

3. The composition of claim 1, further comprising at least one colorant.

4. The composition of claim 1, wherein the oil-dispersible micronized wax constitutes the main wax of the composition.

5. The composition of claim 4, wherein the oil-dispersible micronized wax constitutes at least 80% by weight of the total amount of wax in the composition.

6. The composition of claim 1, wherein the composition is anhydrous.

7. A method of making up lips comprising applying the composition of claim 1 to lips.

8. The composition of claim 1, wherein the volatile hydrocarbon oil is isododecane.

9. The composition of claim 1, further comprising a film forming agent.

10. The composition of claim 1, which is substantially free of silicon oil.

11. The composition of claim 1, comprising 5.5 to 25.75% by weight of the at least one oil-dispersible micronized wax.

* * * * *